United States Patent
Bruecher et al.

(10) Patent No.: US 9,567,356 B2
(45) Date of Patent: Feb. 14, 2017

(54) METHOD FOR THE FRACTIONATION OF PHOSPHO-LIPIDS FROM PHOSPHOLIPID-CONTAINING MATERIAL

(71) Applicant: Cargill, Incorporated, Wayzata, MN (US)

(72) Inventors: Tobias Bruecher, Hamburg (DE); Johan Demey, Brasschaat (BE); Matthias Katte, Hamburg (DE); Jeff Molnar, Bellbrook, OH (US); Susanne Tirok, Hamburg (DE)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 14/437,711

(22) PCT Filed: Oct. 24, 2013

(86) PCT No.: PCT/US2013/066590
§ 371 (c)(1),
(2) Date: Apr. 22, 2015

(87) PCT Pub. No.: WO2014/066623
PCT Pub. Date: May 1, 2014

(65) Prior Publication Data
US 2015/0291637 A1    Oct. 15, 2015

(30) Foreign Application Priority Data

Oct. 24, 2012 (EP) .................................. 12007299

(51) Int. Cl.
*C07F 9/10* (2006.01)
*A23J 7/00* (2006.01)
(Continued)

(52) U.S. Cl.
CPC ................. *C07F 9/103* (2013.01); *A21D 2/32* (2013.01); *A23D 9/013* (2013.01); *A23D 9/04* (2013.01);
(Continued)

(58) Field of Classification Search
CPC ............. C07F 9/103; C07F 9/11; C11B 1/102; A23J 7/00; B01D 11/048; B01D 2011/002
See application file for complete search history.

(56) References Cited

U.S. PATENT DOCUMENTS 4,357,353 A * 11/1982 Strauss ..................... A23J 7/00
514/786
5,214,171 A * 5/1993 Dijkstra ................... A23J 7/00
554/83
(Continued)

FOREIGN PATENT DOCUMENTS

CH          47577          7/1969
CH         475777     *    7/1969
(Continued)

OTHER PUBLICATIONS

CH 475777, Koenig, P. et al., A method for continuously extracting soluble components form pasty, mushy or fine powdery substances, 1969, English translation, 4 pages.*
(Continued)

*Primary Examiner* — Yate K Cutliff

(57) ABSTRACT

The present invention relates to a counter-current extraction process involving a plurality of mixing and separation stages for fractionating a phospholipid-containing feed material into two or more fractions enriched in one or more phospholipids, comprising (a) contacting the phospholipid-containing starting material under agitation with an extractant comprising an aliphatic alcohol selected from C1 to C3
(Continued)

alcohols; (b) separating the obtained emulsion into a phospholipid-enriched extract from a residual raffinate.

14 Claims, 3 Drawing Sheets

(51) Int. Cl.
- *C07F 9/11* (2006.01)
- *A23D 9/04* (2006.01)
- *B01F 17/00* (2006.01)
- *C11B 1/10* (2006.01)
- *A21D 2/32* (2006.01)
- *A23D 9/013* (2006.01)
- *B01D 11/04* (2006.01)
- *B01D 11/00* (2006.01)

(52) U.S. Cl.
CPC ............... *A23J 7/00* (2013.01); *B01D 11/048* (2013.01); *B01D 11/0488* (2013.01); *B01F 17/0064* (2013.01); *C07F 9/10* (2013.01); *C07F 9/11* (2013.01); *C11B 1/102* (2013.01); *A23L 33/12* (2016.08); *A23V 2002/00* (2013.01); *B01D 2011/002* (2013.01)

(56) References Cited

U.S. PATENT DOCUMENTS

| | | |
|---|---|---|
| 2003/0054084 A1 | 3/2003 | Hruschka et al. |
| 2005/0215803 A1 | 9/2005 | Abril |

FOREIGN PATENT DOCUMENTS

| | | |
|---|---|---|
| EP | 0749693 A2 | 12/1996 |
| EP | 1607004 A1 | 12/2005 |
| JP | H08-333378 A | 12/1996 |
| JP | H09-000166 A | 7/1997 |
| JP | H09-000167 A | 7/1997 |
| JP | H10-265485 A | 6/1998 |
| WO | 2012139588 A2 | 10/2012 |

OTHER PUBLICATIONS

"Lecithin—its base and application" (in Japanese), p. 165, Saiwai Shobo (1991).

\* cited by examiner

METHOD FOR THE FRACTIONATION OF PHOSPHO-LIPIDS FROM PHOSPHOLIPID-CONTAINING MATERIAL

CROSS-REFERENCE TO RELATED APPLICATION

This application is a national phase application of International Application PCT/US2013/066590, Filed 24 Oct. 2013, entitled METHOD FOR THE FRACTIONATION OF PHOSPHO-LIPIDS FROM PHOSPHOLIPID-CONTAINING MATERIAL, which claims the benefit of European Application No. 12007299.6, Filed 24 Oct. 2012, entitled, which is hereby incorporated by reference in its entirety METHOD FOR THE FRACTIONATION OF PHOSPHO-LIPIDS FROM PHOSPHOLIPID-CONTAINING MATERIAL.

FIELD OF THE INVENTION

The subject invention relates to a method for process for extracting and separating phospholipids from phospholipid-containing materials, and to the thus obtained fractions, and their various uses.

BACKGROUND OF THE INVENTION

Phospholipids are important components of cell membranes of plants, microbes and animals. The term "phospholipid", refers to compounds derived from fatty acids and a phosphate-containing compound attached to glycerol or the amino alcohol sphingosine, resulting in compounds with fat-soluble and water-soluble regions. The term "lecithin" herein is used for mixtures of phospholipids and triglycerides. The main glycerol-containing phospholipids in lecithin are phosphatidyl choline, phosphatidyl inositol, phosphatidyl ethanolamine and phosphatidic acid, further referred to herein as PC, PI, PE, and PA, respectively. The actual composition of phospholipids depends on the source. A further term employed for highly polar components of lecithin are acetone insolubles, further referred to as AI herein. These are lecithin components that are generally insoluble in phospholipid-saturated acetone, which is typically employed to remove neutral triglycerides from crude lecithin.

A number of processes have been developed to fractionate commercially available lecithin, in particular to obtain fractions enriched in phosphatidyl choline.

U.S. Pat. No. 4,235,793 discloses a process for obtaining oily, highly purified phosphatidylcholines from oily raw phosphatides comprising extracting an oily phosphatide extract from the oily raw phosphatide with a solvent selected from the group consisting of lower alcohols and aqueous solutions thereof containing from about 85 to 96 percent alcohol, directly contacting the said oily phosphatide extract with an aluminium oxide adsorbent and recovering the adsorbed phosphatidylcholine therefrom. The process is cumbersome since it requires the use of large amounts of aluminium oxide, and since the treated material also needs to be filtrated to remove adsorbent fines.

WO-A-2005/072477 discloses a method for the separation of phospholipids from a phospholipid containing material, comprising a) combining the phospholipid-containing material and a water soluble aliphatic alcohol, to form a phospholipid-containing fraction; and b) cooling the phospholipid-containing fraction to precipitate the phospholipids. The thus obtained mixture forms two separate fractions, which were separated by gravity, e.g. through centrifugation. The material is then mixed under heating, specifically with isopropanol, n-propanol and mixtures thereof, followed by a cooling step, and the obtained fractions are separated by several centrifugation steps. As a one-stage extraction process, the maximum extract yield of phospholipids is relatively low. Yet further, the process it is not very suitable for a continuous use, and cumbersome due to several centrifugation and reheating and/or cooling steps required.

Accordingly, there remains a need for a process with improved efficiency of phospholipid fractionation, which is also suitable for use on an industrial scale, and in a continuous process.

SUMMARY OF THE INVENTION

Accordingly, in a first aspect, the present invention relates to an extraction process involving a plurality of mixing and separation stages for fractionating a phospholipid-containing feed material into two or more fractions enriched in one or more phospholipids, comprising the following steps:

(a) contacting the phospholipid-containing starting material under agitation with an extractant comprising an aliphatic alcohol selected from $C_1$ to $C_3$ alcohols and mixtures thereof for a period of time sufficient to effectuate the transfer of at least a fraction of the phospholipids into the extractant;

(b) separating the obtained mixture into a phospholipid-enriched extract from a residual raffinate by a process comprising applying centrifugal forces, wherein the phospholipid-enriched extract from each separation stage is at least in part returned to the previous, or further upstream mixing stages, and wherein a final phospholipid-enriched extract is separated from a first residual raffinate.

In a second aspect, the subject invention relates to a phospholipid-enriched extract obtainable according to the process according to any one of the previous claims. In a further aspect, the subject invention relates to a phospholipid-depleted raffinate obtainable according to the process according to any one of the previous claims.

In a further aspect, the subject invention relates to the use of the phospholipid-enriched extract or a phospholipid-depleted raffinate for food products, preferably bakery products, neutraceutical compostions, confectionery, convenience foods, margarines, spreads; animal feed products and/or pharmaceuticals compositions, or as release agents or industrial emulsifiers.

BRIEF DESCRIPTION OF THE FIGURES

These and further features can be gathered from the claims, description and drawings and the individual features, both alone and in the form of sub-combinations, can be realized in an embodiment of the invention and in other fields and can represent advantages, independently protectable constructions for which protection is hereby claimed. Embodiments of the invention are described in greater detail hereinafter relative to the drawings, wherein:

DETAILED DESCRIPTION OF THE INVENTION

Figure 1:
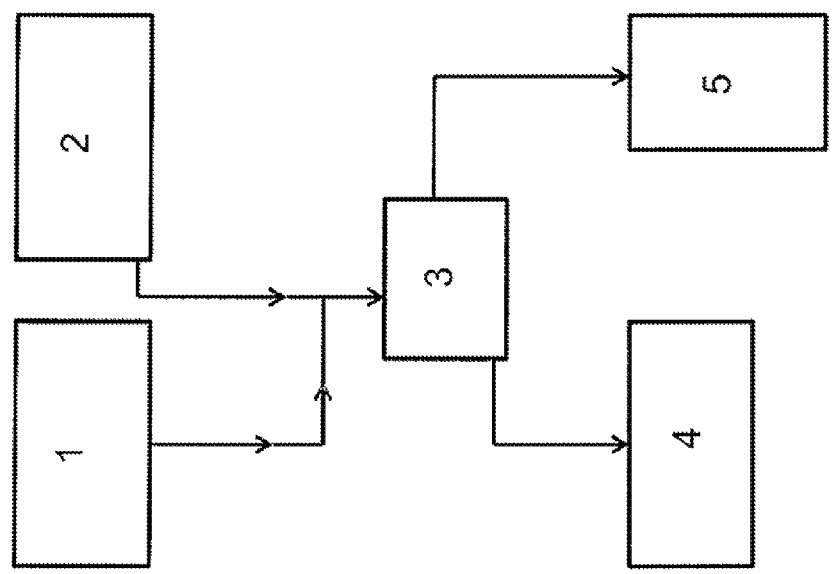
FIG. 1 discloses a schematic diagram of a preferred embodiment of the fractionation process, including peripheral apparatus, as employed in the experiments.

In step (a), the phospholipid-containing starting material is contacted under agitation with an extractant comprising an aliphatic alcohol selected from $C_1$ to $C_3$ alcohols and mixtures thereof for a period of time sufficient to effectuate the transfer of at least a fraction of the phospholipids into the extractant. In the present process, the phospholipid-containing starting material is preferably contacted in (a) with the extractant in a co-current or counter-current mixing operation. While the contact may be co- or counter-current, depending on the manner and apparatus wherein the two liquids are mixed, the overall process flow is counter-current, i.e. the phospholipid-containing starting material is contacted in a first stage with the extractant from a second or further stage, and so on.

In process step (b), the mixture obtained in step (a) is separated by a process involving centrifugal forces.

The term "centrifugal forces" herein refers to the apparent outward force that draws a rotating body away from the centre of rotation. The process preferably is a mechanical process, more preferably by applying the centrifugal force in a rotating device, such as a centrifuge.

The term "mixture" herein refers to any mixture that is obtained in any of the stages of the present extraction process, and includes emulsions and dispersions, and inhomogeneous mixtures and blends. The separation process is preferably executed in a centrifugal device, at a Relative Centrifugal Force (RCF) in the range of from 2 to 25.000 G, more preferably of from 10 to 20.000 G, yet more preferably of from 100 to 18.000 G, and yet more preferably of from 400 to 15.000 G. Since the RCF is positively related with the rotor radius and the rotation speed of a centrifuge, the rotation speed required for a given rotor radius may conveniently be calculated by a skilled artisan.

The extracted phospholipids preferably comprise one or more of phosphatidyl choline (PC), lyso phosphatidyl choline (LPC), phosphatidyl ethanolamine (PE), phosphatidyl inositol (PI) and/or phosphatidic acid (PA). The exact composition of the extracted and residual components largely depends on the starting material, the extractant, and the conditions under which the starting material is extracted, but also the chemical nature of the extractant, and the composition of the extractant phase, e.g. water content and pH value.

The process preferably results in a final raffinate phase comprising less than 20% by weight of phosphatidyl choline (PC), more preferably less than 15% by weight, yet more preferably less than 12% by weight.

More preferably, the final raffinate phase comprises phosphatidyl choline (PC) in an amount in the range of from 1 to 10% by weight, more preferably of from 2 to 9% by weight, and yet more preferably of from 3 to 8% by weight.

The final raffinate phase preferably has an Acetone Insoluble content of from 55 to 75% by weight, more preferably of from 60 to 70% by weight, yet more preferably of from 65 to 70% by weight.

DETAILED DESCRIPTION OF THE DRAWINGS

FIG. 1 depicts a preferred embodiment of the subject process. Herein, a phospholipid feed tank (1) and an extractant tank (2) comprising a heat exchanger (not depicted) are fluidly connected to a multistage centrifugal liquid-liquid extractor (3) having a final extractant outlet (4) and a final raffinate outlet (4). The extractant feed is entered counter-current to the phospholipid feed into the extractor (3), and the final extractant is collected in an exctractant vessel (5) and a raffinate vessel (6). Both tanks (1) and (2) are supplied with flow meters to adjust and control the flow needed for the actual experiment and thus the extraction ratio. Temperature control equipment is installed at the heat exchanger and at both centrifugal extractor inlets and outlets.

Unadjusted lecithin and Ethanol adjusted to water content from 0% to 10% by weight are filled into the tanks (1) and (2), respectively. The Extractant temperature may be adjusted by circulating through the heat exchanger.

Figure 2:
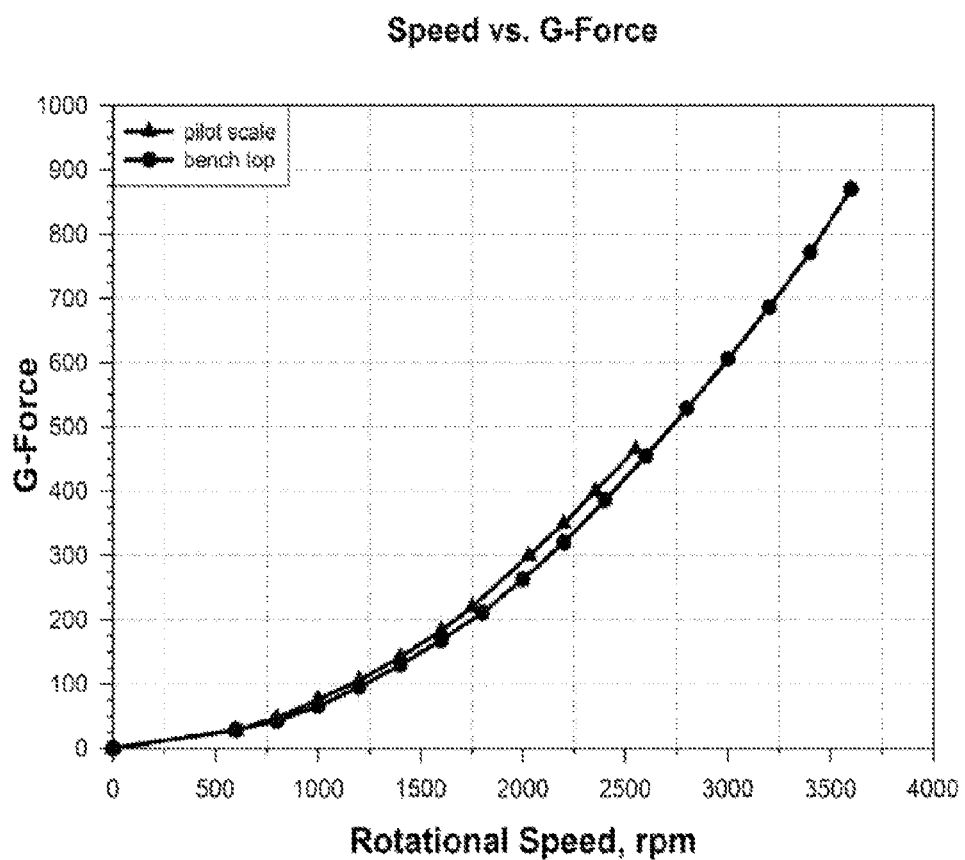
FIG. 2 discloses the ratio of rotation speed versus G-forces applied to mixtures according to a preferred embodiment of the subject process; two different rotors were employed in a centrifugal separator; the X-axis denotes the rotations, as rotations per minute, the Y-axis the G-force.
Figure 3:
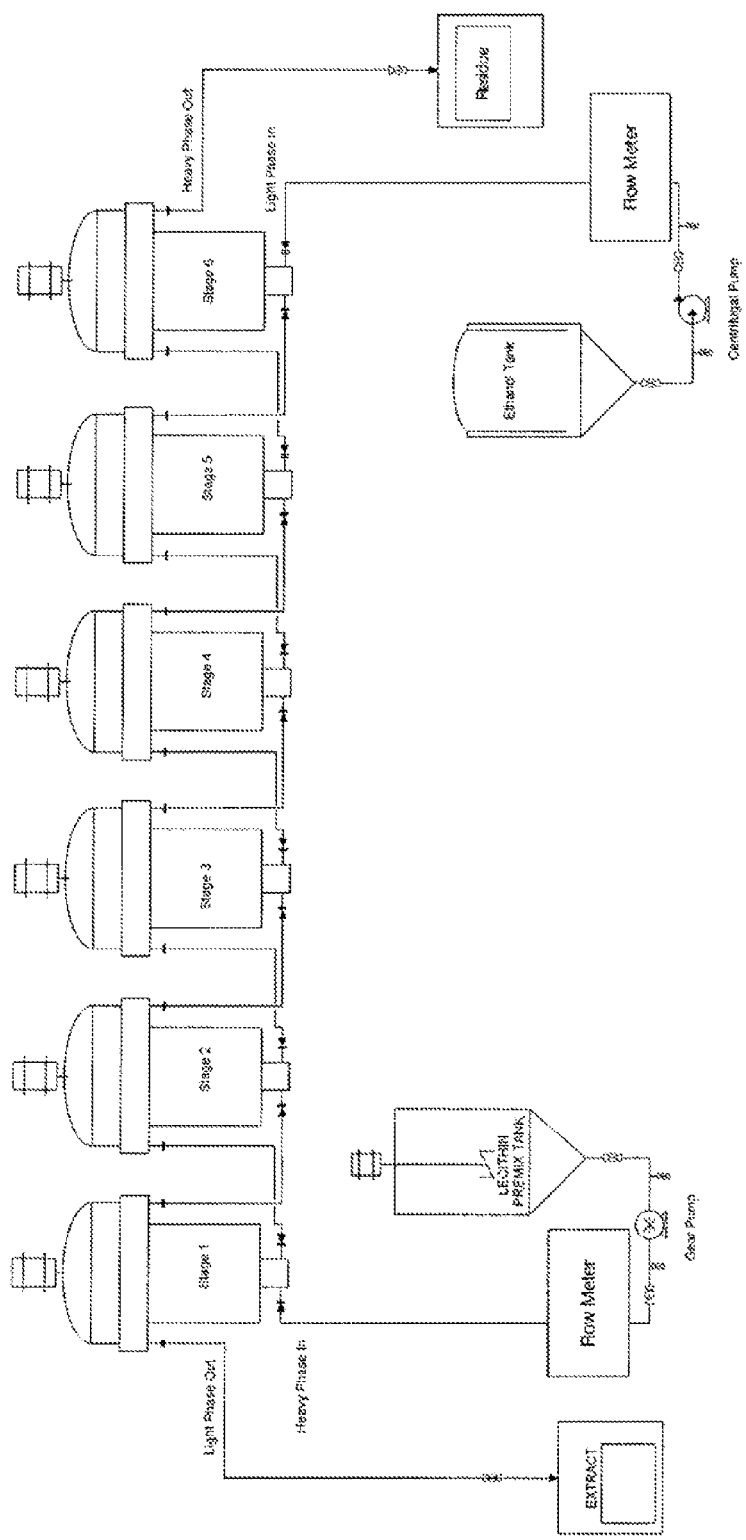
FIG. 3 discloses a schematic line-up of the process in a multistage line-up.

FIG. 2 shows the Relative Centrifugal Force applied for a preferential embodiment of the subject process, whereby a suitable centrifugal device was employed. Herein, two different rotors led to a slight difference in the centrifugal forces that allowed a fast separation.

In the process according to the subject invention, preferably the final extract obtained from the extractant phase comprises at least 25% by weight of phosphatidyl choline (PC), and more than 50% by weight of Acetone Insolubles (AI).

The present process employs a multistage process, i.e. comprising repeated extraction steps, and hence results in a higher yield of desired phospholipids in the extract phase, while simultaneously producing a raffinate phase having a composition significantly different from those typically obtained in the processes disclosed in the prior art.

The phospholipid-containing starting material may be any suitable material, such as crude lecithin of plant or animal origin, oil-derived gums and/or dried gums as obtainable from plant or animal oil and/or fat in degumming processes. Typically, the phospholipid composition of the starting material is in part influenced by the preparation method, however largely defined by the origin of the material.

Suitable lecithin compositions have been disclosed in detail in Kirk-Othmer, Food and Feed Technology, $5^{th}$ Edition, Volume 1, 2007, John Wiley & Sons.

The phospholipid-containing material preferably comprises one or more phospholipids selected from the group consisting of unmodified or chemically modified forms of phosphatidyl choline (PC), LPC, phosphatidyl ethanolamine (PE), Nacylphosphatidyl ethanolamine (NAPE), phosphatidyl serine (PS), phosphatidyl inositol (PI), phosphatidyl glycerol (PG), diphosphatidyl glycerol (DPG), phosphatidic acid (PA), plasmalogen, lecithin and vegetable oil-derived gums. Of these, phosphatidyl choline (PC), phosphatidyl ethanolamine (PE), and phosphatidyl inositol (PI) typically form the majority of the components.

The phospholipid-containing material for use in the subject process may comprise triglyceride oil, or may be partially or completely de-oiled, for instance by acetone or hexane extraction, as disclosed in DE-A-1234680. The presence of the triglycerides was found to not be detrimental for the subject process, since the triglycerides were found hardly soluble in the alcohol extractant employed. Hence the present process advantageously permits the use of crude phospholipid compositions as a starting component. Moreover, the presence of triglycerides in the starting material may reduce the viscosity, and hence may reduce the energy required to achieve a suitable mixing of the extractant phase and the raffinate phase.

Furthermore, addition of oil may advantageously be reduced to the raffinate fraction, thereby reducing the overall volume subjected to the de-oiling step.

Preferred due to the wide availability is plant oil derived lecithin, selected from the group consisting of soybean lecithin, corn germ oil lecithin, rapeseed lecithin including lecithin derived from canola, field mustard and other rapeseed variants and hybrids, rice oil lecithin, sunflower lecithin, cotton seed lecithin, peanut lecithin, coconut oil lecithin, lecithins derived from soybean oil, sunflower oil, rapeseed oil, cottonseed oil, olive oil, corn oil, ground nut or peanut oil, safflower oil, linola oil, linseed oil, palm oil, marine oils, biomass oils derived from other sources than those mentioned herein, and/or coconut oil, and mixtures thereof.

Suitable sources of marine oil lecithins include oils derived from marine life forms such as microalgae or cyanobacteria. Alternatively, animal-based lecithin may be employed, including egg yolk lecithin, milk lecithin and/or brain lecithin, and or mixtures thereof. The raw material to be fractionated is preferably chosen in function of the fraction or fractions required. If a phospholipid fraction that is virtually free from linolenic acid moieties is desired, sunflower lecithin, cottonseed lecithin or corn germ oil lecithin may advantageously be used. For applications requiring a fraction with not too high in unsaturated fatty acid residues, and hence enhanced oxidative stability, rapeseed lecithin may preferably be employed as starting material. Soybean lecithin is strongly preferred due to the availability and its high PC content.

If a phospholipid-comprising mixture, which may further comprise triglycerides and other components normally associated with its isolation and/or preparation, is blended with an aliphatic alcohol under agitation, typically a two-phase system is formed, which upon on settling yields an alcohol-containing, lighter, upper layer containing some phospholipids and possibly triglycerides and other alcohol soluble components, and a phospholipid-containing lower layer containing the remainder of the triglycerides, along with some alcohol.

The standard methods of analysis for the components disclosed herein are according to the European Council Directive No 95/2/EC of 20 Feb. 1995 on food additives other than colours and sweeteners.

While settler/mixer units may be employed to separate extractant and raffinate phases, the separation due to normal gravity is slow, and requires careful control of the temperatures of the liquids. Yet further, the heavier phase tends to have a comparatively high viscosity, making the separation difficult, and leading to a loss in extract yield.

Applicants have now found that if the density separation at each stage is enhanced by increasing the gravitational forces by using one or more centrifugal extractors, while also increasing the energy put into emulsifying the phospholipid phase, the extraction yield of the described phospholipids may be strongly increased, while at the same time the time required to perform the extraction and phase separation is strongly reduced.

Moreover, the thus obtained lighter extracted fraction and the heavier raffinate fraction were found to have different compositions from those typically obtained in the extraction process using mixer/settler units, thereby enhancing the potential for different uses.

Applicants have further found the distribution of the various components over both phases is primarily governed by the phospholipid-containing material; phospholipid-containing material to extractant ratio, the phospholipid composition, the temperature and the extractant composition, especially its water content and/or the acid value, as well as the mechanical agitations supplied to form the liquid/liquid emulsion.

The multi-component system makes a selective fractionation difficult, since the extraction of the different components of the starting material may change when the different parameters are varied. In general, the extractant phase contains more phospholipids at elevated temperatures, at reduced water content.

The present process preferably employs a multistage mixing and liquid/liquid separation apparatus or device. The process according to the invention may be carried out as a batch process, but preferably is executed in a continuous operation. Additionally to centrifugal devices, also mixer/settler systems may advantageously be used.

In the liquid-liquid two-phase extraction process according to the invention, extractant and material to be extracted are introduced into a multistage extraction apparatus. The multistage extraction apparatus preferably has a first inlet and a second inlet. The introduction of both liquids is preferably performed in a counter-current direction to each other, i.e. the lighter phase may advantageously be introduced at the top of the multistage separation device, in the first inlet, while the phospholipid containing material may advantageously be introduced at the bottom, i.e. the second inlet.

In each stage, preferably a mixture of the feed to be extracted and of the extractant preferably may be cycled through a mixer and an overflow vessel, and a quantity of the mixture of solvent and substance may be withdrawn from the overflow vessel at each stage, and separated in a centrifuge into extract and raffinate.

The raffinate is then preferably introduced into the following extraction stage or moved to a further processing step from the final stage, whereas the extract is returned to a preceding stage, or discharged from the first stage into a further processing step. Accordingly, the present process preferably comprises introducing a feed comprising the phospholipid-containing material into a multistage extraction apparatus in a first direction; introducing an extractant comprising an aliphatic alcohol selected from $C_1$ to $C_3$ alcohols and mixtures thereof, which extractant flows through the multistage extraction apparatus in a second direction and forms an extract phase of the fractionation process; contacting the feed and the extractant under agitation; wherein the second direction is counter-current to the first direction.

A particularly suitable multistage extraction apparatus comprises for each stage i) a rotor, ii) a mixing chamber connected to the rotor, and wherein the two liquid streams are mixed, and wherein the mixing chamber comprises iia) a stationary agitator placed in the mixing chamber, and iib) a settling chamber in which the liquid streams are separated by the centrifugal force generated by the mixing chamber. The stationary agitator preferably comprises a stationary disc, and wherein the mixing is achieved through the speed differential between the stationary disc and the rotating mixing chamber. The disc may also act as a pump, thereby moving the extract and raffinate phases through the multistage apparatus.

Both raffinate and extract were found to comprise a different composition of phospholipids, and quite different from those obtained in other known processes, and may thus be useful for different purposes, including food products, more preferably bakery products, neutraceuticals, confectionery, convenience foods, margarines, spreads; neutraceuticals and pharmaceuticals. Alternative preferred uses include cosmetics; animal feed products and/or pharmaceuticals compositions, or as release agents or industrial emulsifiers.

Accordingly the subject invention also relates to the use of the phospholipid-enriched extract or a phospholipid-depleted raffinate for food products, preferably bakery products, neutraceuticals, confectionery, convenience foods, margarines, spreads; animal feed products and/or pharmaceuticals compositions, or as release agents or industrial emulsifiers. Preferably the present process therefore also includes one or more steps for the isolation of the extract or raffinate, and the step of incorporating the extract or raffinate into a product as described herein above.

The extractant comprising the aliphatic alcohol flows through the multistage extraction apparatus in a first direction and contributes to the extractant phase. The material to be extracted flows through the multistage extraction apparatus in a second direction, which second direction is counter-current to the first direction, and contributes to a raffinate phase of the two-phase extraction process.

The two phases are contacted directly, under agitation, to transfer extractable components from the feed into the extractant phase, resulting in an increasingly enriched extractant phase, and an increasingly depleted raffinate phase.

The following, non-limiting examples illustrate the process according to the invention. It should be understood, however, that the invention is not limited to the specific details of the Examples.

Experimental Part

Extractor

A multistage centrifugal liquid-liquid extractor obtained from Rousselet Robatel (France) was employed in the experiments. The extractor comprised 6 rotating bowls, connected to a central rotor, with a maximum rotation speed of 2.900 rpm, and a maximum flow rate (2 phases) of 25 to 30 l/h. The bowls had a useful volume of 0.39 l.

The peripheral equipment was employed according to the schema depicted in FIG. 1. Ethanol was adjusted to a water content from 0% to 10% by weight, and filled into feed tanks. The temperature of the ethanol feed was adjusted by circulating it through a heat exchanger, while the temperatures in the process stages were controlled at the heat exchanger and at both centrifugal extractor inlets and outlets. Both lecithin and ethanol tank were supplied with flow meters to adjust and control the flow needed for the actual experiment and thus the extraction ratio.

At start up, the ethanol flow was adjusted first, and a rotation speed was set. Then the lecithin flow was adjusted.

The system was allowed to stabilize for about 5 min of continuous extract and raffinate outlet flow, and then the actual flows were determined by collecting extract and raffinate phase coming out of the extractor during 5 min and determining weight of the total amount. 5 l of each fraction were collected for further analysis.

Yield Determination:

For yield calculation extract and raffinate streams were collected during 5 minutes and weighed. From that the throughput in kg/h was calculated. Since the extract phase still contained a certain amount of raffinate phase, the raffinate phase content was determined as follows:

A defined amount of well homogenised extract phase was weighed into a centrifuge flask of known weight and centrifuged at 5000 rpm for 10 min (10 C.°). Then the supernatant extract phase was carefully decanted and sediment weighed as raffinate of the homogenized extract phase. The corrected raffinate and extract throughput were then extrapolated from this amount.

Acetone insolubles were determined according to Lange R., Fiebig H. J. (1999): Separation of Phospholipids, Standard Methods of DGF, Fett/Lipid 101: 77-79.

This method is based on the solubility of lecithin components such as triglycerides, fatty acids, sterols, and other acetone-soluble components, and the insolubility of the phospholipids and glycophospholipids in acetone under the test conditions. The latter are termed acetone insolubles (AI).

Generally, about 5 g of a lecithin sample is repeatedly vigorously mixed with about 40 ml of acetone at 0° C. Acetone soluble components are dissolved, while insoluble components precipitate. The precipitates are then filtered off, and washed with acetone, and the residue is dried. The method is repeated at least 4 times, or until no soluble components are detected in the acetone. The amount of the combined residues is considered as the acetone insoluble part of the lecithin sample, and the weight percentage is calculated, by subtracting the content of acetone-soluble components and the water content.

Compositional Data:

An aliquot of the well homogenised extract and raffinate, respectively, were weighed into a round bottom flask of known weight. The solvent was removed in a rotary evaporator at 50-60° C. and reduced pressure, automatically adjusting pressure according to vapour pressure. A final drying step was performed in a freeze-dryer until constant weight was achieved. Dry mass and total yield were calculated from the corrected throughput and dry mass.

Chemical Composition:

Dried samples of extract, with residual raffinate content removed, and of the raffinate phase were analysed for their AI content and acid value. The phospholipid composition was determined using a liquid-chromatographic method.

The identification and quantification of the various phospholipid components may conveniently be executed by different methods, including thin-layer chromatography (TLC), high performance liquid chromatography (HPLC) and $^{31}P$ nuclear magnetic resonance spectroscopy ($^{31}P$-NMR) for the phospholipids only. Suitable methods are disclosed in London E., Feigenson G. W. (1979): Phosphorous NMR Analysis of Phospholipids in Detergents, J. Lipid Res. 20: 408-412; Aitzetmüller K. (1984): HPLC and Phospholipids, Part I: General Considerations, Fette, Seifen, Anstrichm. 86: 318-322; and Aloisi J. D., Sherma J., Fried B. (1990): Comparison of Mobile Phases for Separation and Quantification of Lipids by One-Dimensional TLC and Preadsorbent High Performance Silica Gel Plates, J. Liq. Chromatogr. 13:3949-3961.

Examples 1 to 8

Crude soya lecithin was extracted with ethanol, comprising 2.5% wt. and 4.5% wt. water, respectively. Table 1 depicts the conditions that were applied results of various runs:

TABLE 1

Applied conditions

| Ex. | Extract. stages | T [°] | Water in Ethanol [%] | Extraction Ratio Extractant to Raffinate | Rotation speed |
|---|---|---|---|---|---|
| 1 | 4 | 30 | 4.5 | 1 | 2900 |
| 2 | 4 | 30 | 4.5 | 1 | 2300 |
| 3 | 6 | 12 | 4.5 | 1 | 2300 |
| 4 | 6 | 12 | 4.5 | 1 | 2900 |
| 5 | 6 | 12 | 2.5 | 2 | 2300 |
| 6 | 6 | 12 | 2.5 | 2 | 2900 |
| 7 | 4 | 12 | 2.5 | 1 | 2900 |
| 8 | 4 | 12 | 2.5 | 1 | 2300 |

The obtained extract and raffinate phases were dried to remove volatiles extractant and water, and analysed for acetone insolubles, acid value and composition (see Table 2). The extraction ratio refers to the weight ratio of extractant and raffinate employed in each stage.

TABLE 2

Dried extract and raffinate composition

| | Dried Extract | | | Dried Raffinate (ISOL) | | | | | |
|---|---|---|---|---|---|---|---|---|---|
| Ex. | % AI | % PC | Acid Value | % AI | % PA | % PC | % PE | % PI | Acid Value |
| 1 | 58.7 | 40.9 | 16.6 | 66.8 | 5.3 | 8.0 | 18.6 | 15.9 | 21.2 |
| 2 | 54.2 | 39.5 | 18.4 | 66.1 | 4.6 | 13.2 | 16.9 | 12.4 | 19.5 |
| 3 | 57.5 | 41.1 | 17.6 | 66.4 | 5.0 | 9.2 | 17.5 | 14.6 | 20.7 |
| 4 | 56.4 | 39.3 | 17.2 | 66.7 | 5.0 | 8.6 | 17.8 | 13.2 | 20.5 |
| 5 | 53.4 | 35.2 | 16.5 | 68.1 | 5.2 | 9.2 | 18 | 14.2 | 20.8 |
| 6 | 54.1 | 34.7 | 15.7 | 68.7 | 5.4 | 6.5 | 18.7 | 14.4 | 21.7 |
| 7 | 53 | 36 | 16.9 | 66.9 | 4.8 | 12.8 | 18.6 | 12.8 | 20.1 |
| 8 | 51.5 | 37.8 | 17.4 | 67.1 | 4.7 | 12.8 | 17.5 | 12.3 | 20.1 |

The examples illustrate that using multistage counter-current centrifugal extraction process, it is possible to achieve yields of up to 40% of an ethanol soluble fraction of lecithin showing a high PC content and an adequate PC/AI ratio.

The corresponding raffinate phase is strongly depleted in PC, and has a composition that would typically only be achieved from performing single stage ethanol extraction of previously de-oiled lecithin.

The obtained raffinate fractions were found in particular useful as emulsifiers for food products. In the experiments, it was found that a higher extraction ratio, i.e. extract to raffinate ratio increased the AI content in the raffinate. Higher ethanol temperature also led to increased AI in raffinate, as did a lower water concentration in the ethanol. Both factors appear to enhance triglyceride extraction with the ethanol. While the PC content in raffinate could be reduced by applying a higher extraction ratio, this was also obtained from higher temperature, more extraction stages and increased rotor speed.

Further, a higher extraction ratio, higher temperature and a reduction of the water content in the ethanol also lead to an increase of PA, PI and PE concentrations in the raffinate.

Higher water concentration and higher temperature of the ethanol were found to increase the PC content in the extract, while increasing the extraction ratio led to a lower PC content in the extract.

The invention claimed is:

1. A counter-current extraction process involving a plurality of mixing and separation stages for fractionating a phospholipid-containing starting material into two or more fractions enriched in one or more phospholipids, comprising the following steps:
    (a) contacting the phospholipid-containing starting material under agitation with an extractant comprising an aliphatic alcohol selected from $C_1$ to $C_3$ alcohols and combinations thereof for a period of time sufficient to effectuate the transfer of at least a fraction of the phospholipids into the extractant to obtain a mixture;
    (b) separating the obtained mixture into a phospholipid-enriched extract from a residual raffinate by a process comprising applying centrifugal forces, wherein the phospholipid-enriched extract from each separation stage is at least in part returned to a previous, or further upstream mixing stage, and wherein a final phospholipid-enriched extract is separated from a first residual raffinate, and wherein a final raffinate phase is obtained having between 55 and 75 wt % of Acetone Insolubles (AI).

2. A process according to claim 1, wherein in step (a) the phospholipid-containing starting material is contacted with the extractant in a co-current or counter-current mixing operation.

3. A process according to claim 1, wherein the extracted phospholipids comprise one or more of phosphatidyl choline (PC), phosphatidyl ethanolamine (PE), phosphatidyl Inositol (PI) and/or phosphatidic acid (PA).

4. A process according to claim 1, wherein the final raffinate phase comprises less than 12% by weight of phosphatidyl choline (PC).

5. A process according to claim 1, wherein the final phospholipid-enriched extract comprises at least 25% by weight of phosphatidyl choline (PC).

6. A process according to claim 1, wherein the aliphatic alcohol is ethanol.

7. A process according to claim 1, wherein the aliphatic alcohol has a water concentration that is in the range of from 0 to 10% by weight.

8. A process according to claim 1, wherein steps (a) and (b) are executed at least in part in a multistage extraction apparatus comprising for each stage:
    i) a rotor,
    ii) a mixing chamber connected to the rotor, and wherein two liquid streams are mixed, and wherein the mixing chamber comprises
        iia) a stationary agitator placed in the mixing chamber, and
        iib) a settling chamber in which the liquid streams are separated by the centrifugal force generated by the mixing chamber.

9. A process according to claim 8, wherein the stationary agitator comprises a stationary disc, and wherein the mixing is achieved through speed differentials between the stationary disc and the rotating mixing chamber.

10. A process according to claim 1, comprising at least two extraction and separation stages, wherein the respective extractant is added to the respective raffinate at one or more stages in a counter-current or co-current manner.

11. A process according to claim 1, wherein the final phospholipid-enriched extract and the final raffinate phase are in a weight ratio that is in the range of from 1 to 5, wherein the phospholipid-enriched extract comprises water in an amount of from 1 to 10% by weight, wherein the extractant phase has a temperature of from 25° C. to 70° C., and wherein from 2 to 10 extraction stages are employed using of from 2 to 20.000 g for the separation step.

12. The process according to claim 1, wherein the phospholipid-containing feed comprises lecithin.

13. The process according to claim 12, wherein the lecithin is selected from the group consisting of soybean lecithin, corn lecithin, rapeseed lecithin, rice oil lecithin, sunflower lecithin, cotton seed lecithin, palm oil lecithin, marine oil lecithin, biomass lecithin, peanut lecithin, egg yolk lecithin, milk lecithin and/or brain lecithin.

14. The process according to claim 1, further comprising isolating at least part of the phospholipids from the raffinate and/or extract phase.

* * * * *